United States Patent [19]

Benak et al.

[11] Patent Number: 5,014,695
[45] Date of Patent: May 14, 1991

[54] KIDNEY COOLING JACKET

[76] Inventors: Arnold M. Benak, 270 Evelyn Ave., Toronto, Ontario, Canada, M6P 2Z9; Jaime V. Villamater, 3490 Nadine Crescent, Mississauga, Ontario, Canada, L5A 3L6

[21] Appl. No.: 426,180

[22] Filed: Oct. 25, 1989

Related U.S. Application Data

[63] Continuation-in-part of Ser. No. 212,307, Oct. 4, 1988, abandoned.

[51] Int. Cl.$^5$ .......................... A61F 7/00; A61F 7/12
[52] U.S. Cl. .................................. 128/400; 128/401; 165/46
[58] Field of Search .................... 128/399, 400, 401; 165/46

[56] References Cited

U.S. PATENT DOCUMENTS

| | | | |
|---|---|---|---|
| 3,091,242 | 5/1963 | Johnson, Jr. et al. | 128/402 |
| 3,717,199 | 2/1973 | Dienst | 128/401 |
| 3,738,372 | 6/1973 | Shioshvili | 128/402 |
| 3,830,676 | 8/1974 | Elkins | 128/403 |
| 4,108,146 | 8/1978 | Golden | 128/402 |
| 4,149,541 | 4/1979 | Gammons et al. | 128/402 |
| 4,154,245 | 5/1979 | Daily | 128/401 |
| 4,259,961 | 4/1981 | Hood | 128/401 |

Primary Examiner—Edward M. Coven
Assistant Examiner—Mark S. Graham
Attorney, Agent, or Firm—Blake, Cassels & Graydon

[57] ABSTRACT

The invention concerns a cooling/warming jacket pad for the containment of physiological organs such as hearts and kidneys during medical procedures. The pad when unused is a substantially flat, slim pad having an interior compartment in the form of a passage such that cooling fluid flows past substantially all interior surfaces and null patches of flow are at least mitigated. The pad has an inlet tube and an outlet tube preferably located to minimize interference with a surgeon or surgeons. Portions of the pad may be wrapped over each other to form a cone-shaped jacket within which the organ is contained. The pad may be shaped so that the narrow end of the jacket is open so that physiological tissues and tubes, e.g. blood vessels may project therethrough for connection to like tissues and tubes of a patient while the organ is still within the jacket. To provide this opening the flat pad may have a bay between the wrap-over portions.

4 Claims, 4 Drawing Sheets

KIDNEY COOLING JACKET

This application is a continuation-in-part of application Ser. No. 212,307, filed Oct. 4, 1988 now abandoned.

BACKGROUND OF THE INVENTION

1. Field of the Invention

This invention relates to a cooling jacket to receive physiological organs such as kidneys.

2. Background of the Invention

The ever-increasing frequency of organ surgery, including transplants lays more and more emphasis on the need to maintain the condition of in vitro and transplant organs. This is dependent primarily on lowering the organ temperature in order to achieve low organ metabolism.

Owing to the need to work with the organ within the body of the patient, a number of critical restraints are placed upon the formulation of the cooling/warming device to be used.

Often an organ for transplant must be held in vitro for long periods, for example, during transport from one hospital to another. Moreover, during the surgical process itself, it is important to maintain the organ for transplant in a condition of hypothermia until the latter stages of surgery. Thus, hypothermia should be maintained while the organ is located in the body cavity, while vessels, such as arteries, veins, urethra, etc. are connected and while it is fixed in position. Only immediately prior to start up should the temperature be allowed to rise to body temperature.

The positioning and connection procedures may take a considerable amount of surgical time and have been hampered by the presence of bulky cooling means for the organ. Moreover, cooling means providing uniform cooling over all parts of the organ have raised problems. Still further, cooling jackets of a great variety of different sizes have been necessary since, not only are different sizes necessary for different organs but may also be necessary for similar organs of different sizes. Thus, while it is clear that a heart and a kidney are of considerably different sizes, it may come as a surprise to the layman that kidneys or hearts or other organs may each come in markedly different sizes.

The following listed U.S. Pat. Nos. and article pertain to organ cooling devices:

| | | |
|---|---|---|
| 3,717,199 | February 20, 1973 | Dienst |
| 4,108,146 | August 22, 1978 | Golden |
| 4,416,281 | November 22, 1983 | Cooper et al |
| 4,154,245 | May 15, 1979 | Daily |
| 4,259,961 | April 7, 1981 | Hood |
| 4,474,016 | October 2, 1984 | Winchell |
| 4,530,220 | July 23, 1985 | Nambu et al |

Article "Perfusion" 1986 1: 289-292, published October, 1986.

The patented devices of the prior art suffer from individual drawbacks that include rigidity, unsuitable shape and size, non-uniformity of cooling, clumsiness, and organ non-conformity.

In the case of the device described in the Perfusion article, the coolant path is highly convoluted, and subject to flow stagnation points. Furthermore, this device is intended for use with human hearts, forming a cone shaped pocket to accommodate the cone-like shape of the ventricle.

SUMMARY OF THE INVENTION

According to one aspect of the invention, there is provided a heat exchange jacket comprising a pair of substantially flat, pliant, overlaid sheets sealed together at peripheral margins thereby providing a hollow interior compartment, an inlet for heat exchange fluid into the compartment, an outlet for heat exchange fluid from the compartment, an elongate seal between the paired sheets defining an elongate flow path for heat exchange fluid between the inlet and the outlet, spot seals between the paired sheets in the flow path, and the paired sheets being formable into a cone of variable size having an open wide top end and an open narrow end, having an aperture by overlapping variable opposing portions of the paired sheets.

The passage is such that fluid, for example, cooling liquid, may flow past substantially all interior surfaces and null patches of flow are at least instigated.

Preferably, within the flow passage are located a plurality of spaced spot welds or seals interconnecting the two facing sheets, to limit ballooning of the pad and to maintain the slimness of the pad while permitting suitable flow of heat exchange fluid substantially precluding stagnation in the flow of the fluid through the passage.

The pad may comprise symmetrical wrap-around portions. Suitably, the sheet may be substantially oval, the wrap around portions lying to either side of the minor axis. Preferably, the wrap around portions are partially divided by a symmetrical bay. This bay, when the pad is in cone configuration, may form an opening in the narrow end of the cone through which physiological tissues and tubes, e.g., blood vessels, may protrude. Thus, such vessels or other tissue may be connected to like vessels of the recipient patient with the organ in the cone, within the body cavity of the patient. The slimness of the pad may be advantageous in this respect.

The bay may have a narrow neck so that good overlap is provided at the narrow end of the cone and tabs may be provided extending from the margins in the narrow neck area located to overlay one another in the cone configuration. An additional clip or stitch may be used to secure the overlying tabs together.

At the edge of the pad forming the wide end of the cone, an extension may be provided, which, in use, may be bent over the wide end of the cone to form a cover for the wide end. Suitably, the extension is symmetric with the wrap-over portions and opposite the bay, if present. The extension may adjoin the pad by way of a necked portion, to accommodate the wrapping around of the pad adjoining side portions in forming the pocket, wherein the cover portion does not become unduly distorted as a consequence of that wraparound.

The external tube connections may suitably be adjacent to one another for convenience in use. Moreover, when the tube connections are close together, an elongate passage may easily be provided by providing the elongate seal adjoining the margin between the connections and extending it in the general direction of the major axis of the flat pad. The sealed margins of the sheets may be wide enough, at least over potentially overlying portions, for use as a base for attachment means such as stitches or clips to stabilize the cone, once sufficient wrap-around has been achieved. Thus, in use, the pad may be wrapped into a cone about the organ and placed within a patient's body, having the attached veins and the like protruding from the narrow end. The cone may then be stabilized by a single stitch or clip in the overlying margins of the wide end of the cone. An additional stitch or clip may be placed in the overlying tabs at the narrow end, if these tabs are present.

The elongate seal may comprise at least two smoothly curved interior branches walls dividing the space between the walls into a flow passage substantially uniform cross-section. The spot welds, in addition to maintaining the slim shape of the pad, may subdivide the flow paths into two or more parallel paths, while permitting lateral pressure equalization.

A flat extension of the cooling passage may be provided at the sealed margins of the sheets which form the wide end of the wrapped over cone. In use, this extension may be bent over the wide end of the cone to form a cover. The flap may have a narrowed portion or neck for fluid flow into a wider portion of the flap.

Suitably, the sheets may be silicone rubber sheets, each having a thickness of between 5-10 mils (0.005 to 0.010 inches). A textured surface of the sheet, at least on the surface intended to be adjacent the organ will allow minimal slippage of the organ in the jacket.

In use, it has been found that in the case of broad kidneys the provision of the extension flap over the cone facilitates the maintenance of preferred hypothermia, while in the case of small kidneys there is less need for the encasing cover.

In use, tests have been carried out on different groups of kidneys, one of which groups utilized a cooling jacket according to the invention, having the temperature thereof maintained at 5°-10° Celsius by way of circulation of cold water therethrough. This group was compared with a control group wherein no form of topical hypothermic protection was provided once the kidney had been removed from ice storage.

It was observed that because of the protection afforded by the subject organ receptacle, the surgeons were under a much reduced time constraint and could work at an optimum rate so as to be able to take time for any difficulties that arose in carrying out the anastamosis.

In the case of the control group, having a mean anastamosis time of 33 minutes, a slow but steady rise in temperature occurred, at 0.55° to 0.60° Celsius per minutes, rising to a mean final temperature of about 23° Celsius, with subsequent delay in exhibiting function. In the case of the group wherein a jacket according to the invention was used, mean anastamosis time extended to 46.5 minutes. However, after an initial slight warming phase wherein the internal temperature of the kidney, as measured by an indwelling microthermocouple rose to about 8° or 9° Celsius, the temperature stabilized at that point, and all of the kidneys of the group, despite the longer anastamosis time, displayed early function.

Thus, in addition to maintaining the condition of the organ at a suitable temperature, the jacket permitted enlengthened medical procedures, in the case of difficult anastamosis, without any deleterious effects upon the organ involved.

BRIEF DESCRIPTION OF THE DRAWINGS

Embodiments of the invention are described by way of example, with reference to the drawings wherein.

DETAILED DESCRIPTION OF PREFERRED EMBODIMENTS

Figure 1:
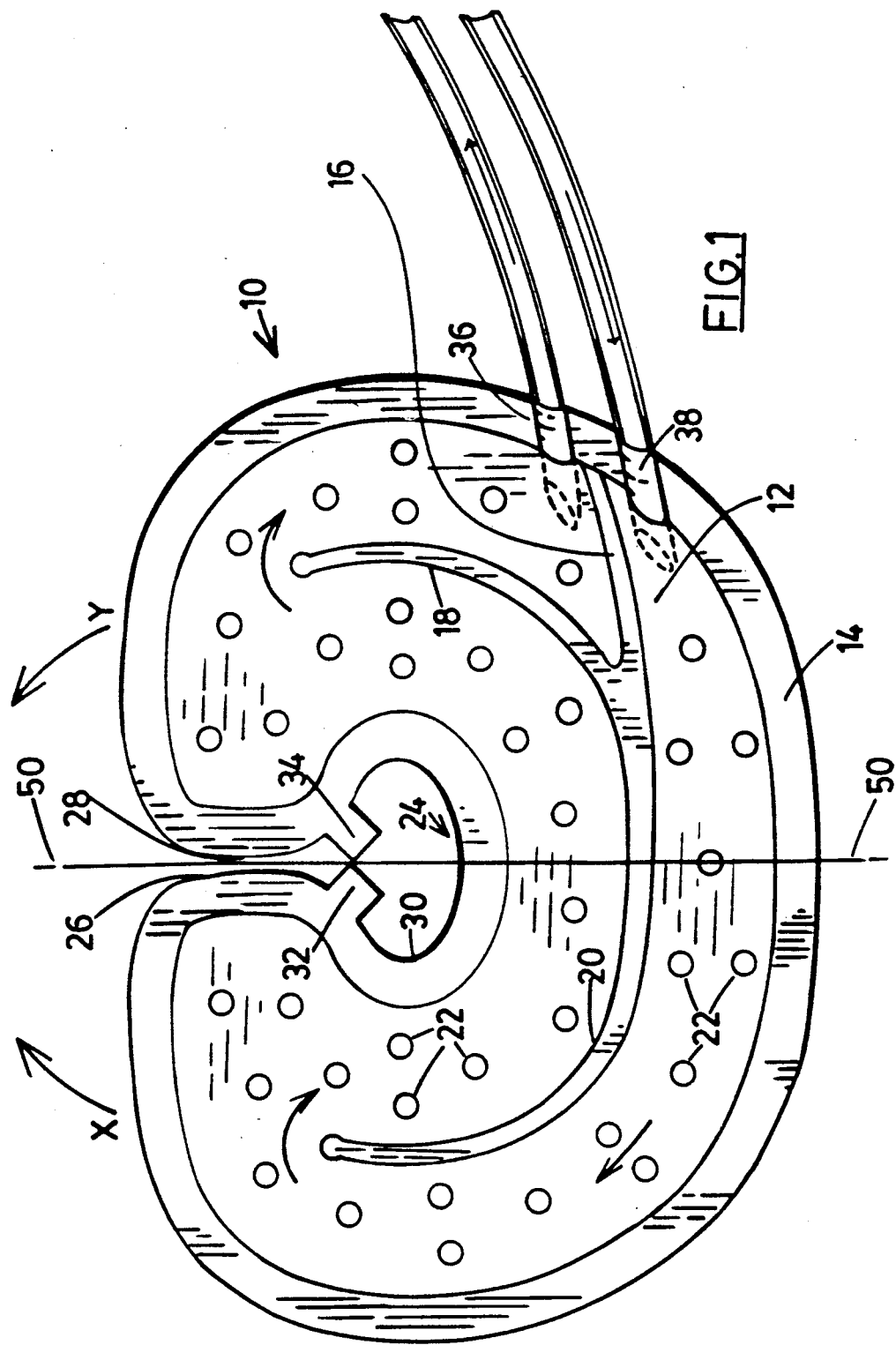
FIG. 1 is a plain view of one jacket according to the invention in flat or storage condition.
Figure 2:
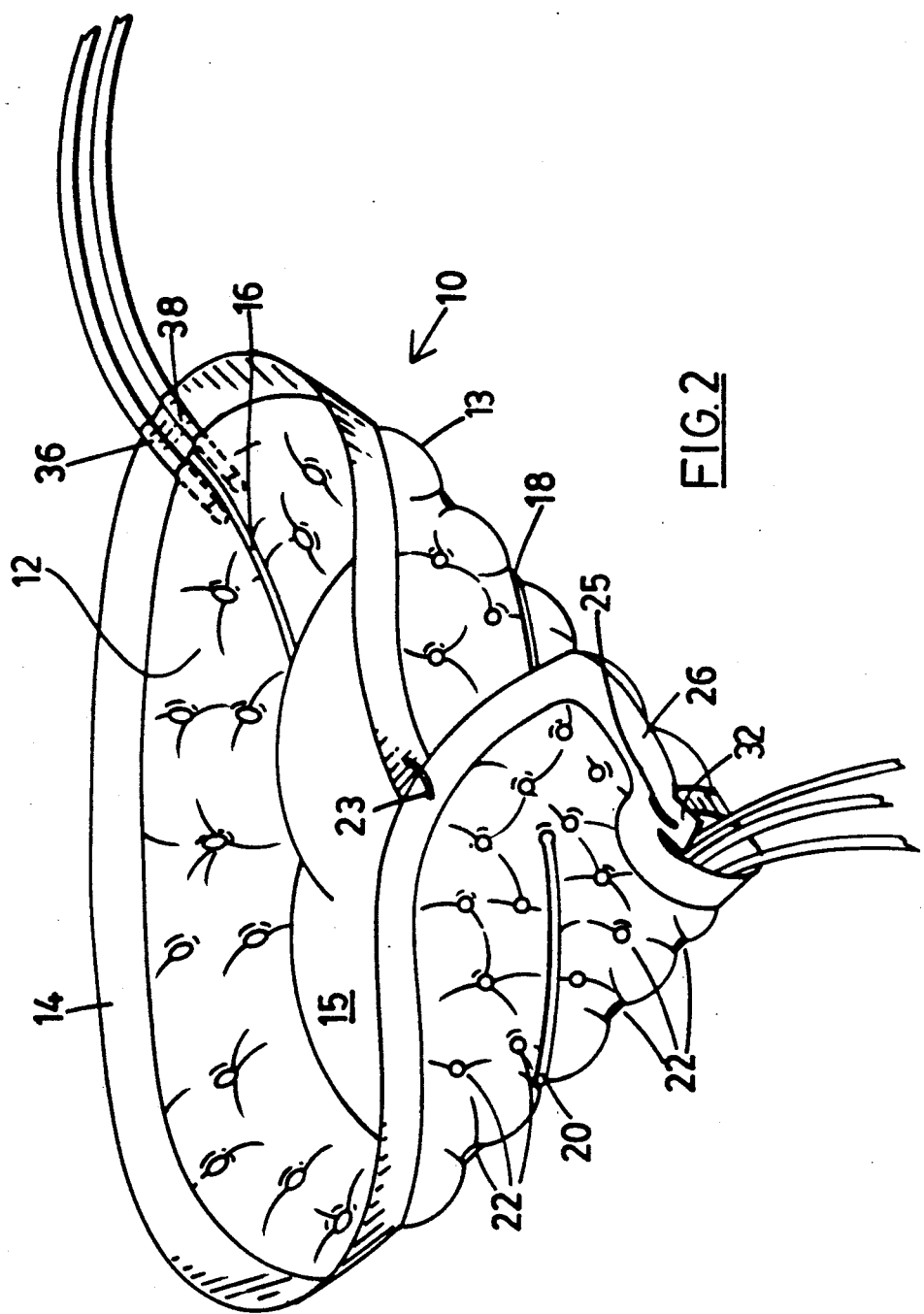
FIG. 2 is a perspective view of the jacket of FIG. 1, in use.

Referring to FIGS. 1 and 2, a jacket 10 comprises a pair of sheets 12 and 13. The sheets are joined together at their peripheral margins 14. A seal between sheets 12, 13 has branches 16, 18 and 20 such that a flow path is defined between the sheets generally as indicated by the arrows in FIG. 1. One end of branch 16 is integral with the sealed margins 14. A plurality of spot seals 22 between sheets 12, 13 are also present to limit the ballooning of the jacket when coolant liquid is flowed through it. A deep re-entrant bay 24 in the periphery of each sheet, having a pair of almost adjoining shoulder portions 26, 28 widens into an enlarged area 30.

In use, the jacket 10 is wrapped to form a cone as shown in FIG. 2. The enlarged area 30 is at the narrow end of the cone and allows for the narrow end of the cone to be open for the passage of vessels of an organ, such as kidney 15 located in the cone-shaped jacket 10. A single stitch, suture or staple 23 in overlapping margins 14 may secure the shape and size of the cone.

For additional security in holding the shape and size of the cone-shaped jacket 10, tabs 32, 34 may be provided at the edge of bay 24 in such positions that they overlap in use and a further single suture 25 may secure them together. These tabs 32, 34 are not necessary and may be omitted. Even when they are provided, for extreme sizes of organ, they may not overlap in use. In such a case, it will not be possible to provide the second suture 25 through the tabs.

Inlet and outlet 38, 36 for coolant are provided to the interior space between sheets 12, 13. An end of inlet tube 38 is located to one side of the branch seal 16 and the end of outlet tube 36 is located to the other side of branch seal 16 so that cooling fluid entering the jacket 10 at inlet tube 38 flows in the direction of the arrows to outlet tube 36 generally reaching all parts of the jacket. Preferably, the seal branches 16, 18, 20 are designed so that the flow rate through all parts of the jacket is similar.

As shown, the sheets 12, 13 and bay 24 are symmetrical about axis 50 but if desired, different shapes may be utilized.

Figure 3:
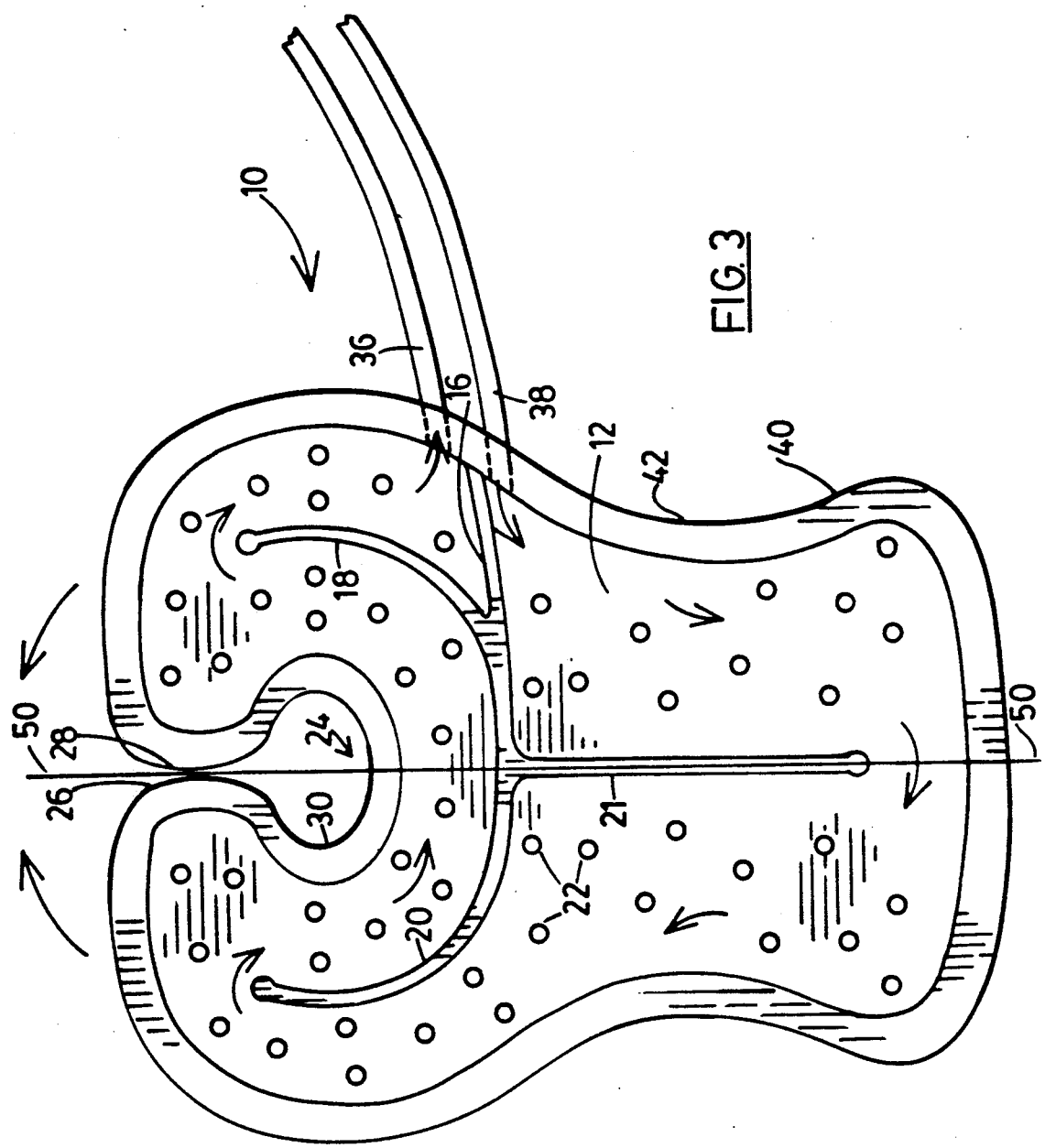
FIG. 3 is a view similar to FIG. 1 of another jacket according to the invention.
Figure 4:
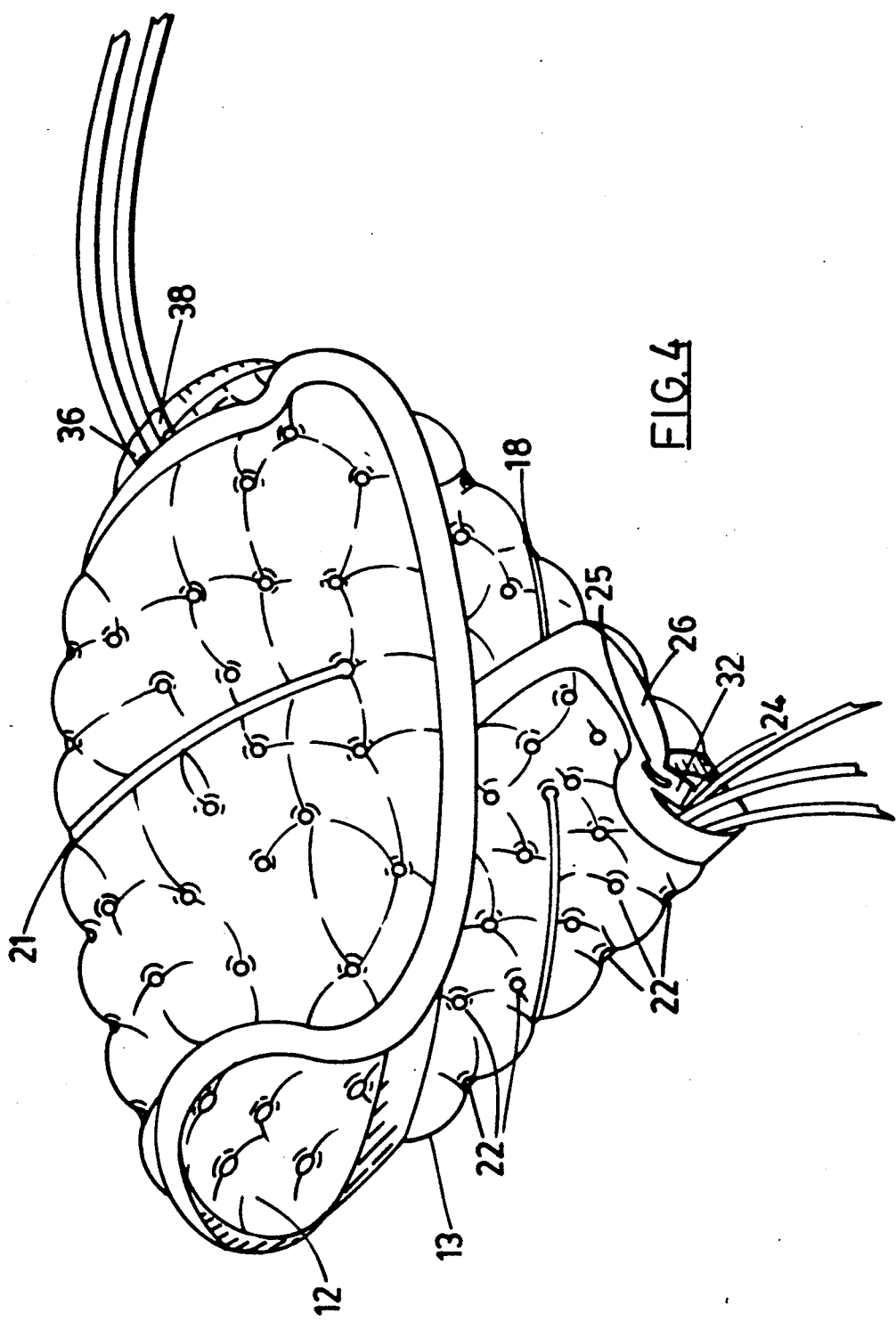
FIG. 4 is a perspective view of the jacket of FIG. 3, in use.

The jacket of FIG. 2 differs from that of FIG. 1 in that it includes a cover flap 40 joining the body of the jacket through a necked portion 42. The jacket 10 including the bay 24 and cover flap 40 may have an axis of symmetry 50 as described for the jacket of FIG. 1. In addition, branch seal 21 also guides coolant liquid through the cover flap, as may be seen from FIG. 3 showing the jacket in use.

In use, the jacket is connected to a closed sterile system, permitting circulation of a chilled normal saline solution or water. Generally, the temperature of the coolant is held between 5° and 11° Celsius. A roller type pump provides low pressure circulation of the coolant without any danger of contamination thereof, in conjunction with a suitable cooling coil.

The minimization of ballooning of the walls of the jacket in combination with the flow path substantially permitting a steady flow rate of coolant through all parts of the jacket, may allow a surgeon to position the jacketed organ directly in the body cavity of a patient and carry out a considerable quantity of the connection surgery with the jacket in place. When removal of the jacket is necessary, it is only necessary to remove or snip suture 23 (and suture 25 if present) permitting total release of the jacket which may then be slid out from beneath the organ with minimum disturbance thereto.

It will be understood that the subject receptacle can be manufactured in a range of sizes, and it is contemplated that changes in shape also may be provided when dealing with specific organs.

We claim:

1. A heat exchange jacket comprising a pair of substantially flat, pliant, overlaid sheets having flush planar faces sealed together at peripheral margins thereby providing an interior compartment having a laminated sheet margin;

an inlet for introducing heat exchange fluid into the compartment;

an outlet for removing heat exchange fluid from the compartment;

an elongate weld between the paired sheets defining an elongate flow path for heat exchange fluid between the inlet and the outlet;

spot welds between the paired sheets in the flow path;

the paired sheets being separable except where sealed to make the jacket turgid by flowing heat exchange fluid therebetween, and being adapted for forming into a cone of variable size having an open wide top end and an open narrow end having an aperture, by overlaying variable opposing portions of the paired sheets; and the paired sheets including a deep peripheral re-entrant bay having a narrowed mouth, the bay being located to form an edge of said open narrow end of said cone when the paired sheets are formed into said cone.

2. A jacket as claimed in claim 1 in which the periphery of the re-entrant bay is provided with tabs adapted to overlap one another when the paired sheets are formed into a cone and which tabs are adapted to be secured together.

3. A jacket as claimed in claim 1 including an extension flap of the overlaid sheets adapted, when the sheet are formed into said cone, to form a cover over said wide top end of the cone.

4. A jacket as claimed in claim 3 in which the extension flap has a neck portion adjoining the body of the jacket and a wider portion distant from the body portion.

* * * * *